(12) United States Patent
Sancho Durá et al.

(10) Patent No.: US 10,113,858 B2
(45) Date of Patent: Oct. 30, 2018

(54) DISTRIBUTED DELAY-LINE FOR LOW-COHERENCE INTERFEROMETRY

(71) Applicant: MEDLUMICS S.L., Madrid (ES)

(72) Inventors: Juan Sancho Durá, Canals (ES); Alberto Martin, Madrid (ES); José Luis Rubio Guivernau, Madrid (ES); Eduardo Margallo Balbás, Madrid (ES)

(73) Assignee: Medlumics S.L., Madrid (ES)

( * ) Notice: Subject to any disclaimer, the term of this patent is extended or adjusted under 35 U.S.C. 154(b) by 0 days.

(21) Appl. No.: 15/237,299

(22) Filed: Aug. 15, 2016

(65) Prior Publication Data

US 2017/0052016 A1 Feb. 23, 2017

Related U.S. Application Data

(60) Provisional application No. 62/207,049, filed on Aug. 19, 2015.

(51) Int. Cl.
*G01B 9/02* (2006.01)
*G02B 6/43* (2006.01)
(Continued)

(52) U.S. Cl.
CPC ..... *G01B 9/02091* (2013.01); *G01B 9/02028* (2013.01); *G01B 9/02051* (2013.01);
(Continued)

(58) Field of Classification Search
CPC .............. G01B 9/02091; G01B 9/0209; G01B 9/02051; G01B 2290/35; G01B 2290/40;
(Continued)

(56) References Cited

U.S. PATENT DOCUMENTS

| 6,198,540 B1 | 3/2001 | Ueda et al. |
| 6,775,007 B2 | 8/2004 | Izatt et al. |

(Continued)

FOREIGN PATENT DOCUMENTS

| EP | 0 675 665 A2 | 10/1995 |
| EP | 1 574 885 A1 | 9/2005 |

(Continued)

OTHER PUBLICATIONS

International Search Report and Written Opinion directed to International Patent Application No. PCT/EP2016/069673, dated Oct. 19, 2016; 13 pages.

*Primary Examiner* — Tarifur Chowdhury
*Assistant Examiner* — Jonathon Cook
(74) *Attorney, Agent, or Firm* — Sterne, Kessler, Goldstein & Fox P.L.L.C.

(57) ABSTRACT

A Time Domain Optical Coherence Tomography system using a modulation scheme multiplexes the scanning range of the delay line into different spectral bands. Such a modulation scheme may allow for power consumption reduction compared with a single delay line element since the same modulation pattern is being used for several channels. In an example, the optical coherence tomography system may include a plurality of stages, each stage having a group delay element. The distinct group delays may be introduced to scan a sample with distinct electrical frequency bands at distinct axial scanning depth ranges.

29 Claims, 6 Drawing Sheets

(51) Int. Cl.
  *G02B 6/12* (2006.01)
  *G02B 6/28* (2006.01)
  *A61B 3/10* (2006.01)
(52) U.S. Cl.
  CPC ....... *G02B 6/12004* (2013.01); *G02B 6/2861* (2013.01); *G02B 6/43* (2013.01); *A61B 3/102* (2013.01); *G01B 2290/35* (2013.01); *G01B 2290/40* (2013.01); *G02B 2006/12142* (2013.01)
(58) Field of Classification Search
  CPC .... G02B 6/12004; G02B 6/2861; G02B 6/43; G02B 2006/12142; A61B 3/102
  USPC .................................................. 356/497, 479
  See application file for complete search history.

(56) References Cited

U.S. PATENT DOCUMENTS

| | | | |
|---|---|---|---|
| 9,113,782 B2 † | 8/2015 | Hogan | |
| 2004/0239938 A1* | 12/2004 | Izatt | G01B 9/02004 356/479 |
| 2010/0039651 A1* | 2/2010 | Gelikonov | A61B 5/0066 356/479 |
| 2010/0119189 A1* | 5/2010 | Nasu | G02B 6/12007 385/1 |
| 2011/0029049 A1* | 2/2011 | Vertikov | A61B 5/14532 607/104 |
| 2011/0134435 A1* | 6/2011 | Chou | A61B 5/0066 356/497 |
| 2012/0022360 A1* | 1/2012 | Kemp | A61B 5/6852 600/410 |
| 2014/0078510 A1* | 3/2014 | Rubio Guivernau | G01B 9/02091 356/479 |
| 2014/0160430 A1 | 6/2014 | Ko et al. | |
| 2014/0368828 A1 | 12/2014 | Soler et al. | |

FOREIGN PATENT DOCUMENTS

| | | |
|---|---|---|
| WO | WO 2012/160005 A1 | 11/2012 |
| WO | WO 2013/001032 A1 | 1/2013 |

\* cited by examiner
† cited by third party

DISTRIBUTED DELAY-LINE FOR LOW-COHERENCE INTERFEROMETRY

This application claims priority to application Ser. No. 62/207,049 filed Aug. 19, 2015, which is hereby incorporated by reference in its entirety.

FIELD

Embodiments of the invention relate to designs of, and methods of using, distributed delay-line for use in an optical coherence tomography system.

BACKGROUND

Optical Coherence Tomography (OCT) is a medical imaging technique providing depth-resolved information with high axial resolution by means of a broadband light source and an interferometric detection system. OCT has found plenty of applications, ranging from ophthalmology and cardiology to gynecology and in-vitro high-resolution studies of biological tissues.

Traditionally, axial information in OCT is obtained through interferometric methods. Time Domain Optical Coherence Tomography (TD-OCT) utilizes a variable path length in the interferometric detection system that changes in time. Thus, one of the elements in a TD-OCT system may be a variable delay line, which may be used to perform the depth scan (or axial scan) inside the sample. Several publications have described implementations of delay lines that are able to provide the necessary delay variation range at high scan speeds for their use in OCT.

For example, WIPO Patent Application Publication No. 2013/001032 A1, which is incorporated by reference herein in its entirety, describes a proposed multiplexing scheme that spreads the light into paths with different lengths using a modulator in at least one of the paths so as to separate them in frequency channels. In this way, the axial scanning distance is increased, avoiding the subsequent scanning increase in the variable delay component.

As occurs with other implementations, such as mechanical or electro-optical delay lines, the bandwidth of the system may restrict the OCT performance in terms of scanning speed. Both phase and amplitude modulation at frequencies close to the bandwidth edges elicit nonlinear behavior. In the particular case of thermo-optical modulators, phase modulation at higher frequencies generates a non-uniform optical phase response along the temperature variation. As a result, the frequency response will experience a broadening.

This broadening of the frequency response complicates the filtering process because adjacent channels will be filtered as well—generating artifacts and double images. In addition, detection bandwidth must be increased in order to recover all scanning information. Unfortunately, noise increases as the detection bandwidth increases and, therefore, the image quality or signal to noise ratio (SNR) decreases.

Working with a linear (but lower modulation) frequency regime complicates the spectrum channel separation, as the filter's order must be high. Scaling the whole system so that the delay line frequency and the modulator's frequency are reduced yields a poor frame rate performance. Although significant improvements have taken place in OCT instrumentation during the last decade, efforts have been focused on imaging speed and quality, and the progress in reduction of cost, size and complexity of systems has been merely incremental. This is believed to be one of the main factors preventing a wider adoption of OCT in emerging clinical applications beyond the well-established one of ophthalmology. Further miniaturization of OCT imaging engines has the potential to promote widespread adoption of the technique and to open a new range of applications.

BRIEF SUMMARY

In order to overcome the aforementioned problem, a modulation scheme based on a variable delay line is proposed by means of frequency multiplexing. Such multiplexing is performed by keeping one modulating frequency, but having different scanning ranges and speeds per channel. The TD-OCT system presented here uses a modulation scheme that multiplexes the scanning range of the delay line into different spectral bands. A modulation scheme may allow for power consumption reduction compared with a single delay line element since the same modulation pattern is being used for several channels.

In an embodiment, an optical coherence tomography system may include an optical source configured to provide a beam of radiation; an optical element configured to direct a first portion of the beam of radiation toward a sample arm and a second portion of the beam of radiation toward a reference arm; and a detector configured to receive the first and second portions of the beam of radiation from the sample arm and reference arm, wherein the reference arm includes a plurality of stages, each stage having a fixed group delay element and a group delay modulator, wherein group delay element and the group delay modulator are configured to introduce a group delay such that the first portion of the beam of radiation corresponding to a distinct axial scanning depth range interferes with the second portion of the beam of radiation.

In another embodiment, an optical coherence tomography system may include an optical source configured to provide a beam of radiation; an optical element configured to direct a first portion of the beam of radiation toward a sample arm and a second portion of the beam of radiation toward a reference arm; and a detector configured to receive the first and second portions of the beam of radiation from the sample arm and reference arm, wherein the sample arm includes a plurality of stages, each stage having a fixed group delay element and a group delay modulator, wherein group delay element and the group delay modulator are configured to introduce a group delay such that the first portion of the beam of radiation corresponding to a distinct axial scanning depth range interferes with the second portion of the beam of radiation.

In another embodiment, an optical coherence tomography system may include an optical source configured to provide a beam of radiation; an optical element configured to direct a first portion of the beam of radiation toward a sample arm and a second portion of the beam of radiation toward a reference arm; and a detector configured to receive the first and second portions of the beam of radiation from the sample arm and reference arm, wherein one of the sample arm and the reference arm includes a first plurality of stages, each stage having a fixed group delay element and the other of the sample arm and the reference arm includes a second plurality of stages, each stage having a group delay modulator, and wherein each fixed group delay element and the group delay modulator are configured to introduce a group delay such that the first portion of the beam of radiation corresponding to a distinct axial scanning depth range interferes with the second portion of the beam of radiation.

In another embodiment, a distributed delay line for optical coherence tomography may include a first stage having a first optical coupler configured to receive an input beam of radiation and apportion the input beam onto a first optical path and a second optical path; a first group delay element on a first optical path, the first group delay element configured to introduce a first group delay on a first portion of the input beam of radiation; and a first modulator on the first optical path, the first modulator configured to modify the first group delay introduced on the first portion of the input beam of radiation; and a second stage coupled to the first and second optical paths having a second optical coupler configured to receive the first and second portions of the input beam and apportion a third portion and a fourth portion of the input beam onto a third optical path and a fourth optical path, wherein each the third and fourth portions of the input beam are a combination of the first and second portions of the input beam; a second group delay element on a third optical path, the second group delay element configured to introduce a second group delay on a third portion of the input beam of radiation and being different from the first group delay; and a second modulator on the third optical path, the second modulator configured to modify the second group delay introduced on the first portion of the input beam of radiation.

A distributed delay line for optical coherence tomography may include a first stage having a first optical coupler configured to receive an input beam of radiation and apportion the input beam onto a first optical path and a second optical path; a first group delay element on a first optical path, the first group delay element configured to introduce a first group delay on a first portion of the input beam of radiation; and a first modulator on the second optical path, the first modulator configured to modulate group delay introduced on the second portion of the input beam of radiation; and a second stage coupled to the first and second optical paths, the second stage having a second optical coupler configured to receive the first and second portions of the input beam and apportion a third portion and a fourth portion of the input beam onto a third optical path and a fourth optical path, wherein each of the third and fourth portions of the input beam are a combination of the first and second portions of the input beam; a second group delay element on a third optical path, the second group delay element configured to introduce a second group delay on a third portion of the input beam of radiation and being different from the first group delay; and a second modulator on the fourth optical path, the second modulator configured to modify the second group delay introduced on the fourth portion of the input beam of radiation.

BRIEF DESCRIPTION OF THE DRAWINGS/FIGURES

The accompanying drawings, which are incorporated herein and form a part of the specification, illustrate embodiments of the present invention and, together with the description, further serve to explain the principles of the invention and to enable a person skilled in the pertinent art to make and use the invention.

Embodiments of the present invention will be described with reference to the accompanying drawings.

DETAILED DESCRIPTION

Although specific configurations and arrangements are discussed, it should be understood that this is done for illustrative purposes only. A person skilled in the pertinent art will recognize that other configurations and arrangements can be used without departing from the spirit and scope of the present invention. It will be apparent to a person skilled in the pertinent art that this invention can also be employed in a variety of other applications.

It is noted that references in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases do not necessarily refer to the same embodiment. Further, when a particular feature, structure or characteristic is described in connection with an embodiment, it would be within the knowledge of one skilled in the art to effect such feature, structure or characteristic in connection with other embodiments whether or not explicitly described.

Embodiments described herein provide systems and methods for introducing a group delay to a beam of radiation within an interferometric device. For example, the interferometric device may use low coherence interferometry such as optical coherence tomography (OCT) to provide image data at different depths within a sample. Varying the group delay of the light corresponds to varying a scan depth within the sample under study. Though the embodiments described herein are primarily directed to a modulation scheme for axial scanning, these embodiments may be combined with known lateral scanning systems to generate 3D volumetric images.

In the various embodiments described herein, the group delay is varied by controlling the index of refraction of a waveguide material that is guiding the beam of radiation. This may be achieved, for example, by having a waveguide segment perform multiple passes over at least one region where the refraction index can be controlled by active temperature changes, so that the heat produced by the heating elements is reused. A single pass system, however, may alternatively be utilized with the embodiments described herein. Other techniques beyond generating a heat gradient may be used as well to control the refractive index.

Figure 1:
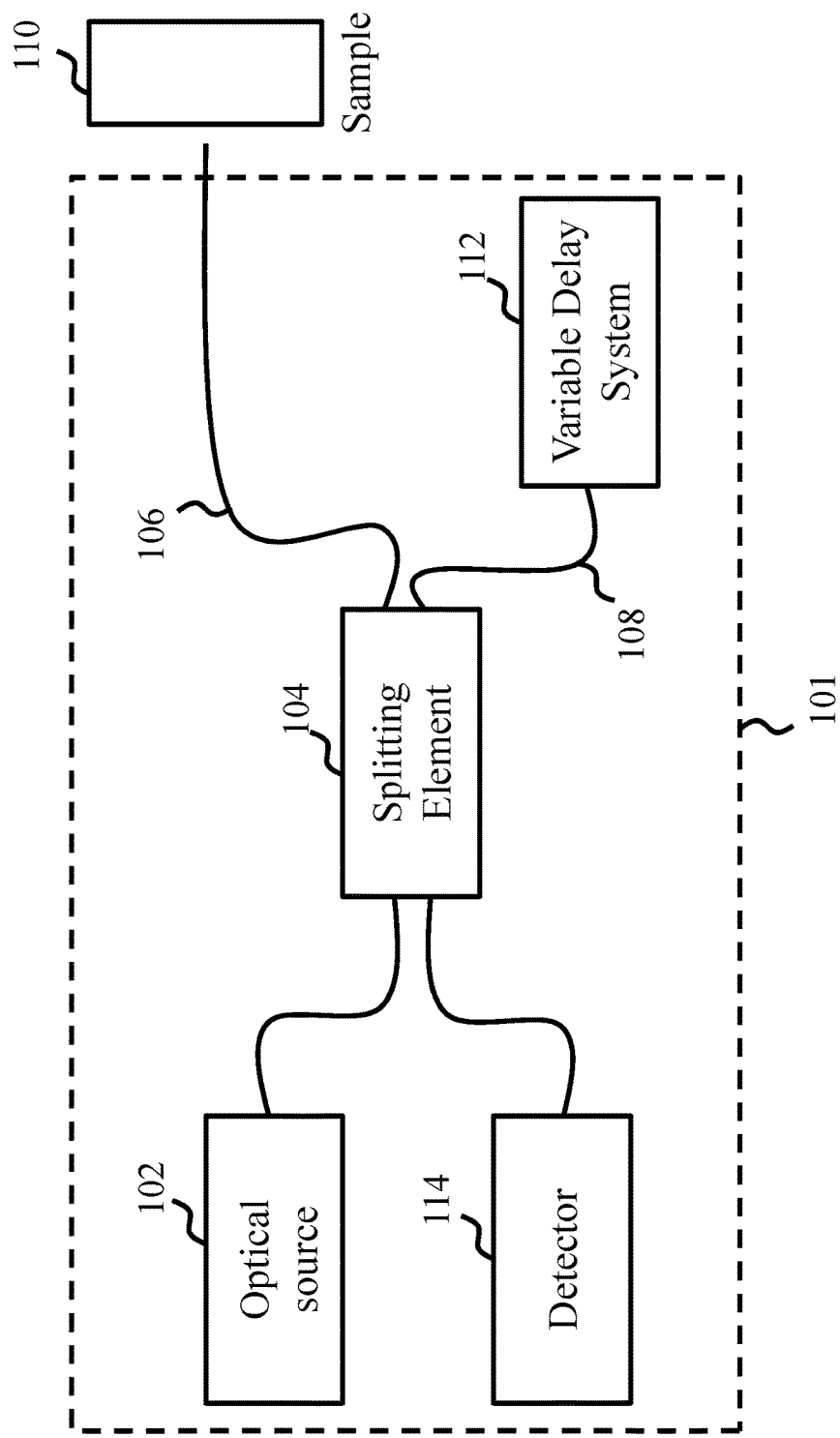
FIG. 1 illustrates a block diagram of a reflective OCT system, according to an embodiment.

FIG. 1 illustrates OCT system 101 including an optical source 102, a splitting element 104, a sample arm 106, a reference arm 108, variable delay system 112, and a detector 114. In the embodiment shown, variable delay system 112 is located within reference arm 108. It should be understood, however, that variable delay system 112 may instead be located in sample arm 106. A simple delay line in sample arm 106 may take advantage of the light delivered to and reflected from the sample. In one example, sample arm 106 and reference arm 108 include optical waveguides such as pattern or rib waveguides or optical fibers.

OCT system 101, utilizing a variable delay system 112, is used for imaging a sample 110, according to an embodiment.

Variable delay system 112 may be used to provide a variable delay to the light within OCT system 101. Light reflected from sample 110 and returned by variable delay system 112 may be processed to form a high-resolution image of the sample, such as a high resolution three-dimensional volumetric image. Herein, the terms "electromagnetic radiation," "light," and "beam of radiation" are all used to describe the same electromagnetic signals propagating through the various described elements and systems.

In an embodiment, all of the components of OCT system 101 are integrated onto a planar lightwave circuit (PLC). In another embodiment, at least all the components within variable delay system 112 are integrated on the same substrate of a PLC. Other implementations may be considered as well, such as, for example, fiber optic systems, free-space optical systems, photonic crystal systems, etc.

It should be understood that OCT system 101 may include any number of other optical elements not shown for the sake of clarity. For example, OCT system 101 may include mirrors, lenses, gratings, splitters, micromechanical elements, etc., along the paths of sample arm 106 or reference arm 108. OCT system 101 may include various modulating elements configured to suppress contributions of interference signals generated in non-active optical paths. In another example, OCT system 101 may include MEMS (Micro Electro Mechanical Systems), which apply an additional physical lateral scan to the beams. An optical element in the path of the light may be displaced by electromechanical actuators (e.g. based on thermal expansion, piezoelectric or electrostatic force) that are integrated by means of microfabrication techniques.

Splitting element 104 is used to direct light received from optical source 102 to both sample arm 106 and reference arm 108. Splitting element 104 may be, for example, a bi-directional coupler, an optical splitter, or any other modulating optical device that converts a single beam of light into two or more beams of light.

Light that travels down sample arm 106 ultimately impinges upon sample 110. Sample 110 may be any suitable sample to be imaged, such as tissue. During an OCT procedure, the light scans at a certain depth within sample 110 and the scattered radiation is collected back into sample arm 106. In another embodiment, the scattered radiation is collected back into a different waveguide than the transmitting waveguide. The scan depth may be chosen via the delay imposed on the light within variable delay system 112. Variable delay system 112 may include one or more multiplexing units, with each unit differentiating the light among a plurality of optical channels. More details regarding the various multiplexing units are discussed herein.

Light within sample arm 106 and reference arm 108 is recombined before being received at detector 114. In the embodiment shown, the light is recombined by splitting element 104. In another embodiment, the light is recombined at a different optical coupling element than splitting element 104.

OCT system 101 may provide a distribution of the delay needed in different components, segmenting the axial scanning into Frequency Division Multiplexing (FDM) channels. Thus, OCT system 101 may simultaneously scan a sample at a plurality of axial depths. As a result, OCT system 101 may optimize bandwidth and maximum delay for the TD-OCT variable delay components. In an embodiment, optical source 102 provides broadband light and variable delay system 112 separates the electrical spectrum of the detected signal into distinct channels that axially scan a sample at distinct axial scanning depth ranges and distinct frequency ranges.

Figure 5:
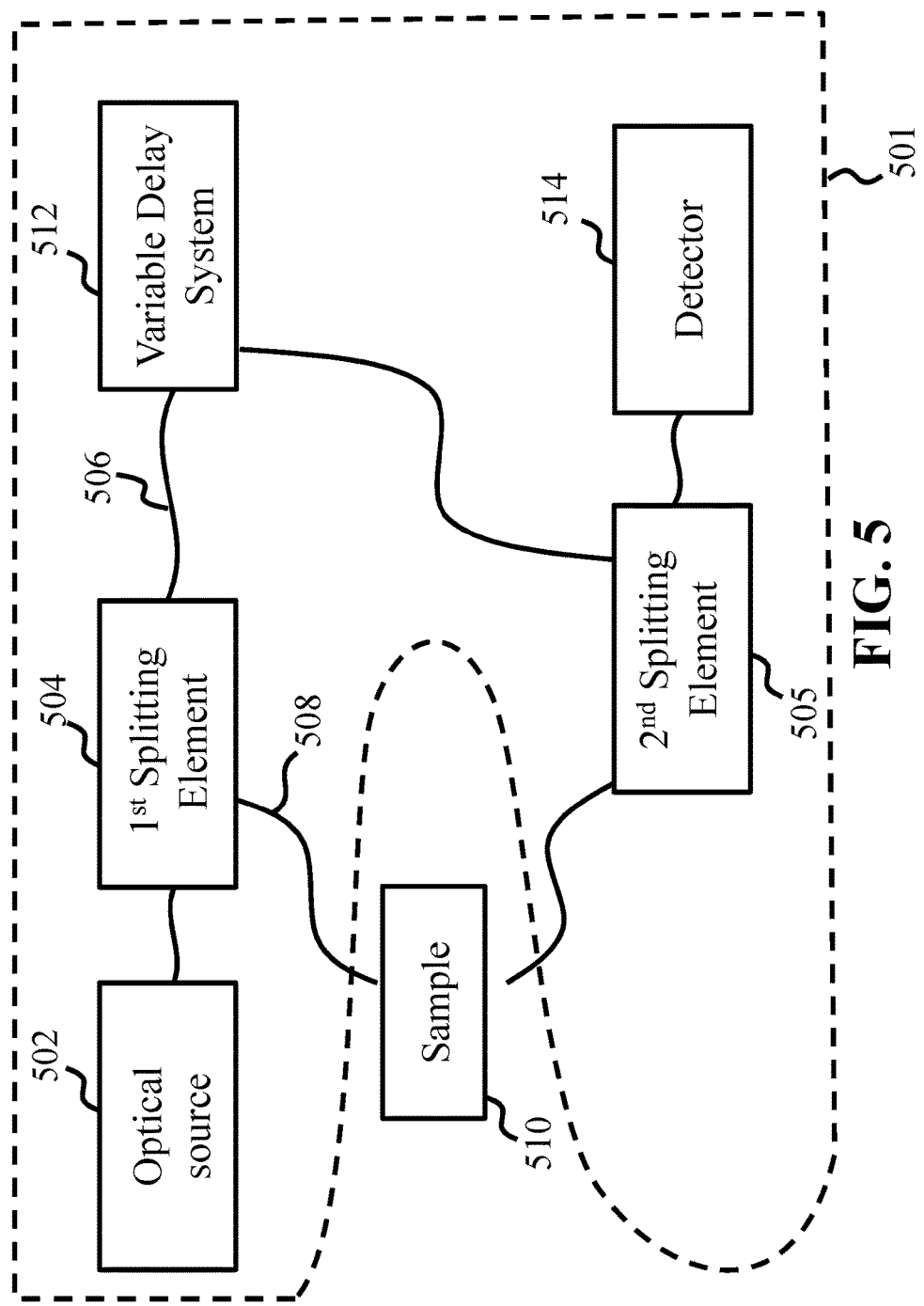
FIG. 5 illustrates a block diagram of a transmissive OCT system, according to an embodiment.

The OCT system may be configured as either a reflective system or a transmissive system. The OCT system 101 illustrated in FIG. 1 is configured as a reflective system, i.e., the detection light is light reflected from the sample. Alternatively, a similar OCT system 501 may be configured as a transmissive system, i.e., the detection light is light transmitted through the sample, as illustrated in FIG. 5. Similar to the reflective configuration illustrated in FIG. 1, the transmissive configuration of FIG. 5 illustrates OCT system 501 including an optical source 502, a first splitting element 504, a sample arm 506, a reference arm 508, variable delay system 512, and a detector 514. In addition, OCT system 501 may include a second splitting element 505 to direct the transmitted light and the light from variable delay system 512 to detector 514. The various details and alternatives of reflective OCT system 101 as described above (as well as those described below) apply respectively to transmissive OCT system 501.

Figure 2:
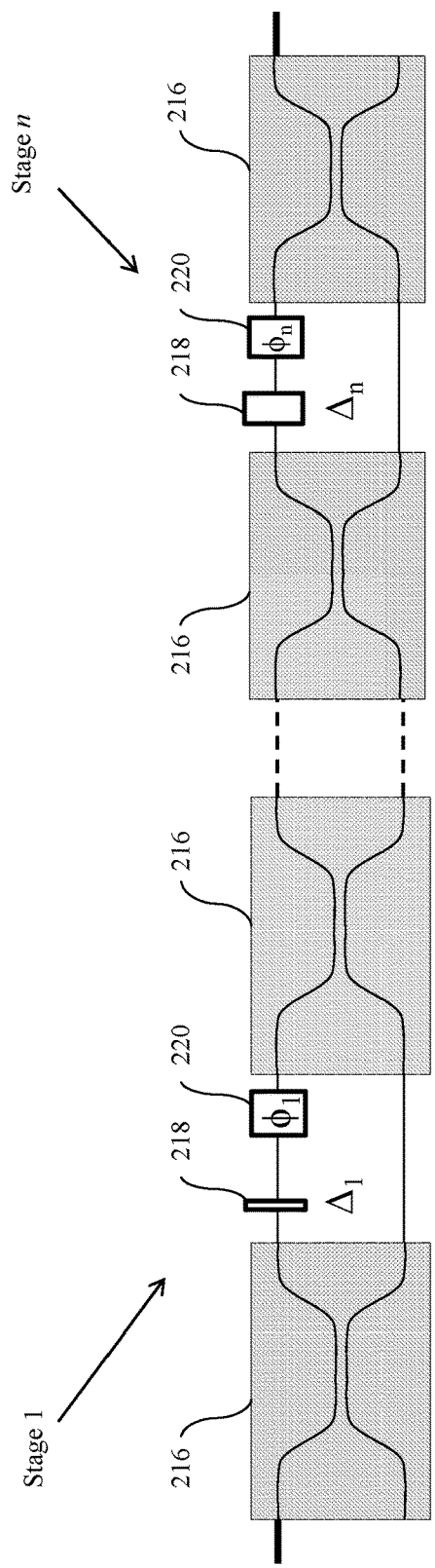
FIG. 2 illustrates an example of multi-stage network for implementing the proposed modulation scheme.

FIG. 2 illustrates an example frequency domain modulation scheme of n number of stages. The modulation scheme presented here mainly refers to the reference arm, but a similar approach can be used in the sample arm. Each stage may include couplers 216, group delay elements 218, and group delay modulators 220. The stages are coupled together to form an interferometric network. The interferometric network divides the axial scanning range into $2^n$ channels. Each one of the stages may have different delays $\Delta_n$ so that the variable delay line in the sample arm can constructively interfere with reference arm at different depths. Varying the group delay of the light corresponds to varying a scan depth within the sample under study. If the stages are arranged in series, the delay needed by a single stage or section is much smaller than the one required by the entire system delay using this architecture and modulation scheme. Thus, exemplary modulation schemes allow for modulator bandwidth optimization.

In one embodiment, frequencies of phase modulation signals applied to the group delay modulators 220 are all the same and equal to the one applied into a delay line in the sample arm. Such phase modulation signals, however, must be inverted with respect to the sample arm signal since the direction of their effect in the axial scanning is opposite. Thus, from the modulators scheme shown in FIG. 2 a frequency domain modulation scheme of $2^n$ channels is obtained (where n is the number of modulator stages or sections).

In an embodiment, couplers 216 may be optical couplers, such as 2×2 fiber optic couplers. In one example, three couplers may be used in series for a total of eight channels. Each channel may be used to scan a sample at a different axial depth. The information from each channel may be extracted and processed to form an image of the sample.

Group delay elements 218 add a group delay in each stage to their respective portion of the optical path. An optical channel having a desired delay may then be formed by adding appropriate delays together along the optical path. In an embodiment, group delays introduced by group delay elements 218 are fixed. Group delay modulators 220 induce a relative change of group delay in each stage such that the combined effect of group delay elements and group delay modulators of a particular optical path corresponds to a distinct axial scanning depth in a sample. The goal is to produce a plurality of possible optical channels, each with a different total group delay. In this manner, a desired group delay can be implemented in the OCT system to image different depths without moving parts.

In an example, each of these optical channels is modulated using a characteristic frequency. Group delay elements 218 may be implemented in a variety of appropriate ways, such as by including waveguide segments of different lengths to physically increase the length of a particular optical path. In an embodiment, each group delay element 218 induces a distinct group delay and the group delay elements 218 are arranged in increasing or decreasing order. In an embodiment, group delay modulators 220 may be thermo-optic modulators. For example, the thermo-optic modulators may be of the type described in WIPO Patent Application Publication No. 2013/001032 A1, which is incorporated by reference herein in its entirety. Such thermo-optic modulators may modulate a beam of radiation by varying the refractive index of a waveguide carrying the beam of radiation.

Figure 6:
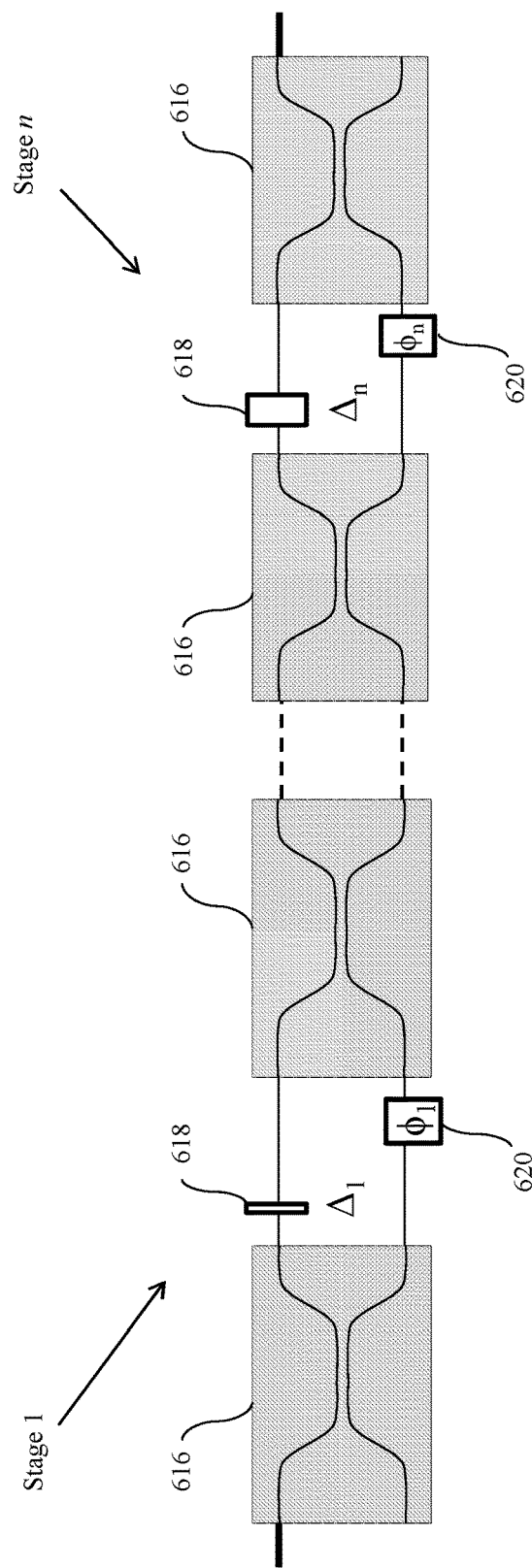
FIG. 6 illustrates another example of multi-stage network for implementing the proposed modulation scheme.

Though the example of the modulation scheme of FIG. 2 shows fixed group delay elements 218 and variable group delay modulator 220 on the same optical path in each stage, group delay elements 218 may be in a separate optical path from the group delay modulators 220. For example, FIG. 6 illustrates a multi-stage network for implementing the proposed modulation scheme with fixed group delay elements 618 and group delay modulators 620 in different paths in each stage of the OCT system. Fixed group delay elements 618 are in a first set of paths that are optically coupled in series in the reference arm, while group delay modulators are in a second set of paths optically coupled in series in the sample arm.

Figure 3:
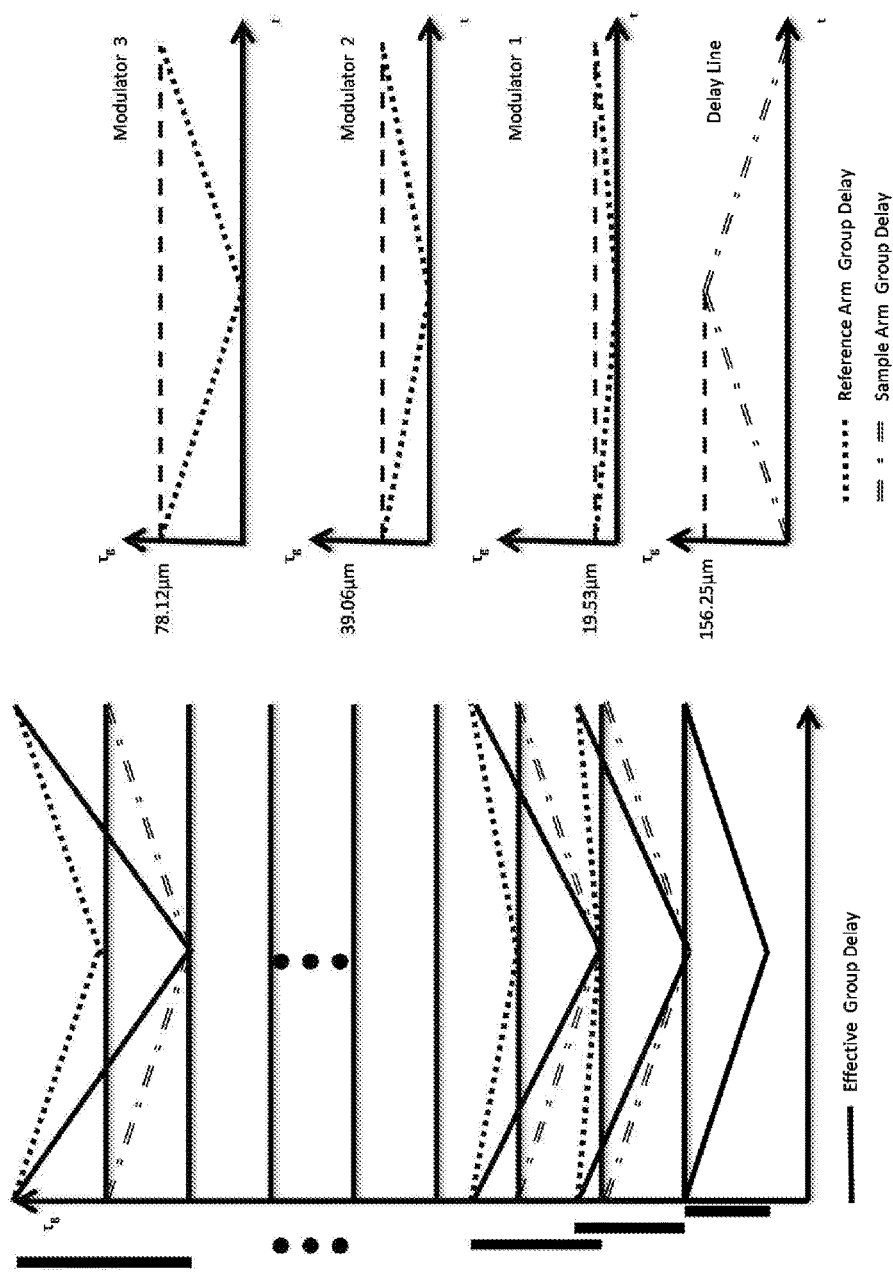
FIG. 3 illustrates an example according to an embodiment of a delay line modulation scheme.

FIG. 3 illustrates an example embodiment of a delay line modulation scheme, with group delay ($\tau_g$) resulting from an example embodiment of a three-stage modulation scheme. Delay waveforms from the sample arm delay line and reference modulators 1 to 3 are depicted on the right. In this example, the sample delay line scans up to 156.25 µm in air, while modulator delays vary from 19.53 µm to 78.12 µm. In order to keep uniform Doppler frequencies separation, delay increases between channels may be uniform. As explained above, modulator waveforms in the reference arm may be inverted with respect to the one in sample arm. The graphs on the left of FIG. 3 illustrate the effective group delay as a consequence of the combination of the sample and reference arm scanning. The largest group delay contribution comes from the delay element in the sample arm. While the additional group delay contributions come from the three modulation stages in the reference arm. The three-stage modulation scheme creates eight different channels with eight different Doppler frequencies.

The example modulators' delay magnitude was chosen so that the Doppler frequencies of the channels are distant enough to be separated in a later processing step. Were it otherwise, inter-channel crosstalk would degrade the image quality of the OCT system. The Doppler frequency is related to the slope of the group delay shown in FIG. 3. In some embodiments, channel distribution may be that in which each modulator's delay amplitude should be more than twice the previous one.

In one embodiment of FIG. 3, the variable delay ranges applied to the modulators create a scanning overlap in some of the generated channels. This means that a particular depth of the sample may be scanned by multiple channels. Despite a loss in energy efficiency, the overlap between channels may be used to increase the signal-to-noise ratio (SNR) by averaging the overlapping signals.

Figure 4:
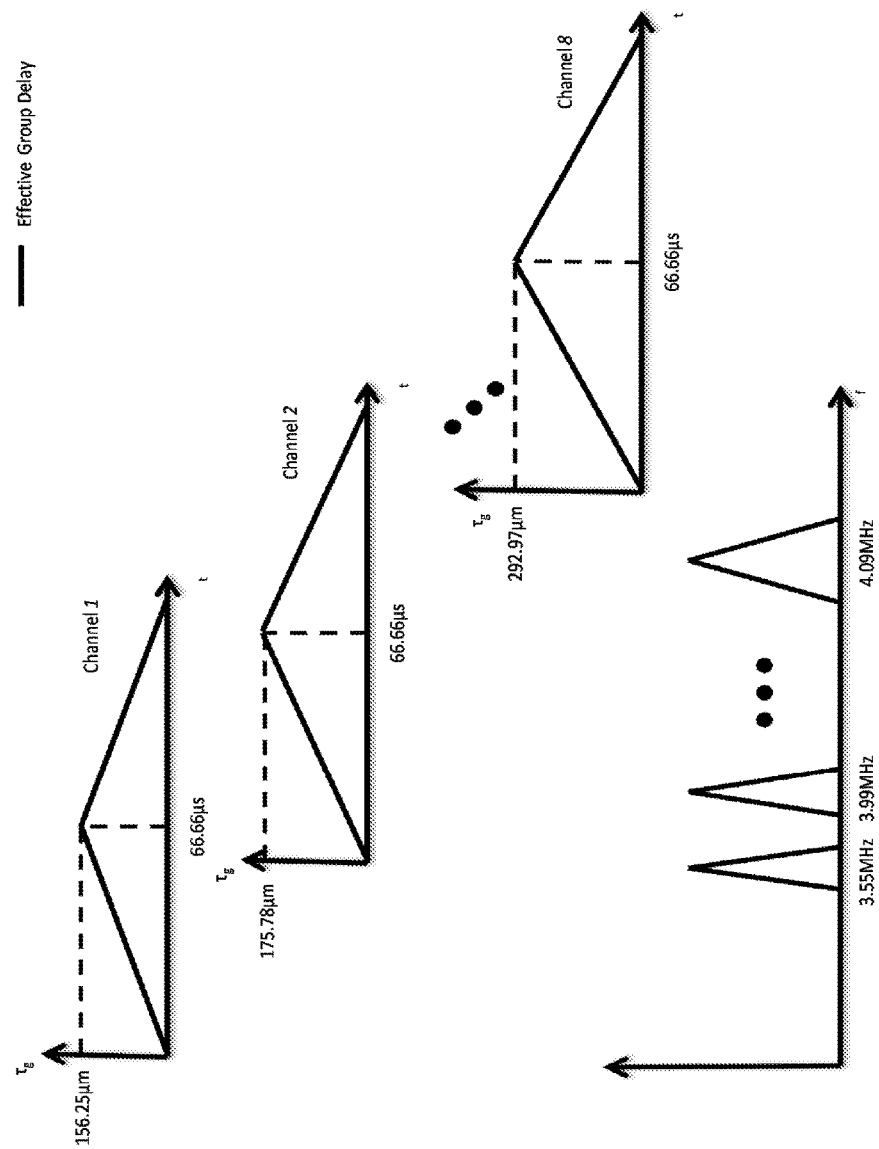
FIG. 4 illustrates an example embodiment of the FDM channels' scanning depth and frequency spectrum.

FIG. 4 shows FDM channels' scanning depth and frequency spectrum. In one embodiment, higher channels (in Doppler frequency) have greater separation than lower channels. Apart from increasing the central frequency for each channel, modulation also increases bandwidth. Higher frequency channels contribute to higher noise since the detection bandwidth increases. Consequently, higher frequency channels will show lower signal-to-noise ratio (SNR) or image quality compared to lower frequency channels. An embodiment may, therefore, use low frequency channels for deeper areas and high frequency channels for swallow areas to equalize the overall image quality. Alternatively, an embodiment may use high frequency channels for deeper areas and high frequency channels for swallow areas.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

Embodiments of the present invention have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. An optical coherence tomography system comprising:
    an optical source configured to provide a beam of radiation;
    an optical element configured to direct a first portion of the beam of radiation toward a sample arm and a second portion of the beam of radiation toward a reference arm; and
    a detector configured to receive the first and second portions of the beam of radiation from the sample arm and reference arm,
    wherein the reference arm includes a plurality of stages, each stage having a fixed group delay element and a group delay modulator, wherein the fixed group delay element and group delay modulator are configured to introduce a group delay such that the first portion of the beam of radiation corresponding to a distinct axial scanning depth range interferes with the second portion of the beam of radiation, wherein frequencies of phase modulation signals applied to each group delay modulator are the same and equal to a phase modulation frequency applied to a delay line in the sample arm.

2. The optical coherence tomography system of claim 1, wherein the sample arm and the reference arm are implemented using silicon-on-insulator (SOI) technology.

3. The optical coherence tomography system of claim 1, wherein the stages are coupled together in series via optical couplers.

4. The optical coherence tomography system of claim 3, wherein the optical couplers are 2×2 optical couplers.

5. The optical coherence tomography system of claim 1, wherein the stages are coupled together to form $2^n$ channels, wherein n is the number of stages.

6. The optical coherence tomography system of claim 5, wherein an effective group delay between channels is uniform.

7. The optical coherence tomography system of claim 1, wherein each group delay modulator comprises a thermo-optic modulator.

8. The optical coherence tomography system of claim 1, wherein the fixed group delay elements in each stage induce a different group delay from the fixed delay elements in the other stages.

9. The optical coherence tomography system of claim 1, wherein two of the distinct axial scanning depth ranges at least partially overlap.

10. An optical coherence tomography system comprising:
an optical source configured to provide a beam of radiation;
an optical element configured to direct a first portion of the beam of radiation toward a sample arm and a second portion of the beam of radiation toward a reference arm; and
a detector configured to receive the first and second portions of the beam of radiation from the sample arm and reference arm,
wherein the sample arm includes a plurality of stages, each stage having a fixed group delay element and a group delay modulator, wherein fixed group delay element and the group delay modulator are configured to introduce a group delay such that the first portion of the beam of radiation corresponding to a distinct axial scanning depth range interferes with the second portion of the beam of radiation, and wherein frequencies of phase modulation signals applied to each group delay modulator are the same and equal to a phase modulation frequency applied to a delay line in the sample arm.

11. The optical coherence tomography system of claim 10, wherein the sample arm and the reference arm are implemented using silicon-on-insulator (SOI) technology.

12. The optical coherence tomography system of claim 10, wherein the stages are coupled together in series via optical couplers.

13. The optical coherence tomography system of claim 12, wherein the optical couplers are 2×2 optical couplers.

14. The optical coherence tomography system of claim 10, wherein the stages are coupled together to form $2^n$ channels, wherein n is the number of stages.

15. The optical coherence tomography system of claim 14, wherein an effective group delay between channels is uniform.

16. The optical coherence tomography system of claim 10, wherein each group delay modulator comprises a thermo-optic modulator.

17. The optical coherence tomography system of claim 10, wherein the fixed group delay elements in each stage induce a different group delay from the fixed delay elements in the other stages.

18. The optical coherence tomography system of claim 10, wherein two of the distinct axial scanning depth ranges at least partially overlap.

19. An optical coherence tomography system comprising:
an optical source configured to provide a beam of radiation;
an optical element configured to direct a first portion of the beam of radiation toward a sample arm and a second portion of the beam of radiation toward a reference arm; and
a detector configured to receive the first and second portions of the beam of radiation from the sample arm and reference arm,
wherein one of the sample arm and the reference arm includes a first plurality of stages, each stage having a fixed group delay element and the other of the sample arm and the reference arm includes a second plurality of stages, each stage having a group delay modulator, and
wherein each fixed group delay element and group delay modulator are configured to introduce a group delay such that the first portion of the beam of radiation corresponding to a distinct axial scanning depth range interferes with the second portion of the beam of radiation, and
wherein frequencies of phase modulation signals applied to each group delay modulator are the same and equal to a phase modulation frequency applied to a delay line in the sample arm.

20. The optical coherence tomography system of claim 19, wherein the sample arm and the reference arm are implemented using silicon-on-insulator (SOI) technology.

21. The optical coherence tomography system of claim 19, wherein the first plurality of stages are coupled together in series via optical couplers and the second plurality of stages are coupled together in series via optical couplers.

22. The optical coherence tomography system of claim 21, wherein the optical couplers are 2×2 optical couplers.

23. The optical coherence tomography system of claim 19, wherein the first plurality of stages are coupled together to form $2^n$ channels, wherein n is the number of stages and the second plurality of stages are coupled together to form $2^n$ channels.

24. The optical coherence tomography system of claim 23, wherein an effective group delay between channels is uniform.

25. The optical coherence tomography system of claim 19, wherein each group delay modulator comprises a thermo-optic modulator.

26. The optical coherence tomography system of claim 19, wherein the fixed group delay elements in each stage induce a different group delay from the fixed delay elements in the other stages.

27. The optical coherence tomography system of claim 19, wherein two of the distinct axial scanning depth ranges at least partially overlap.

28. A distributed delay line for optical coherence tomography, comprising:
a first stage comprising:
a first optical coupler configured to receive an input beam of radiation and apportion the input beam onto a first optical path and a second optical path;

a first group delay element on a first optical path, the first group delay element configured to introduce a first group delay on a first portion of the input beam of radiation; and a first modulator on the first optical path, the first modulator configured to modify the first group delay introduced on the first portion of the input beam of radiation; and a second stage coupled to the first and second optical paths comprising:

a second optical coupler configured to receive the first and second portions of the input beam and apportion a third portion and a fourth portion of the input beam onto a third optical path and a fourth optical path, wherein each of the third and fourth portions of the input beam are a combination of the first and second portions of the input beam;

a second group delay element on a third optical path, the second group delay element configured to introduce a second group delay on a third portion of the input beam of radiation and being different from the first group delay; and a second modulator on the third optical path, the second modulator configured to modify the second group delay introduced on the third portion of the input beam of radiation, wherein frequencies of phase modulation signals applied to the first modulator are the same and equal to frequencies of phase modulation signals applied to the second modulator.

29. A distributed delay line for optical coherence tomography, comprising:

a first stage comprising:

a first optical coupler configured to receive an input beam of radiation and apportion the input beam onto a first optical path and a second optical path;

a first group delay element on a first optical path, the first group delay element configured to introduce a first group delay on a first portion of the input beam of radiation; and a first modulator on the second optical path, the first modulator configured to modulate group delay introduced on the second portion of the input beam of radiation; and a second stage coupled to the first and second optical paths comprising:

a second optical coupler configured to receive the first and second portions of the input beam and apportion a third portion and a fourth portion of the input beam onto a third optical path and a fourth optical path, wherein each of the third and fourth portions of the input beam are a combination of the first and second portions of the input beam;

a second group delay element on a third optical path, the second group delay element configured to introduce a second group delay on a third portion of the input beam of radiation and being different from the first group delay; and a second modulator on the fourth optical path, the second modulator configured to modify the second group delay introduced on the fourth portion of the input beam of radiation, wherein frequencies of phase modulation signals applied to the first modulator are the same and equal to frequencies of phase modulation signals applied to the second modulator.

* * * * *